(12) United States Patent
Leue

(10) Patent No.: US 9,561,087 B2
(45) Date of Patent: Feb. 7, 2017

(54) DISCHARGING DEVICE

(71) Applicant: Sulzer Mixpac AG, Haag (CH)

(72) Inventor: Percy Leue, Singen (DE)

(73) Assignee: SULZER MIXPAC AG, Haag (CH)

( * ) Notice: Subject to any disclaimer, the term of this patent is extended or adjusted under 35 U.S.C. 154(b) by 7 days.

(21) Appl. No.: 14/649,391

(22) PCT Filed: Nov. 12, 2013

(86) PCT No.: PCT/EP2013/073654
§ 371 (c)(1),
(2) Date: Jun. 3, 2015

(87) PCT Pub. No.: WO2014/086559
PCT Pub. Date: Jun. 12, 2014

(65) Prior Publication Data
US 2015/0342706 A1 Dec. 3, 2015

(30) Foreign Application Priority Data

Dec. 4, 2012 (EP) .................................... 12195468

(51) Int. Cl.
*A61C 5/06* (2006.01)
*B65D 83/00* (2006.01)
*B05C 17/01* (2006.01)
*A45D 34/04* (2006.01)

(52) U.S. Cl.
CPC .............. *A61C 5/062* (2013.01); *A45D 34/04* (2013.01); *B05C 17/012* (2013.01); *B05C 17/0116* (2013.01); *B05C 17/0133* (2013.01); *B65D 83/0005* (2013.01); *B65D 83/0033* (2013.01); *A45D 2200/055* (2013.01)

(58) Field of Classification Search
CPC ............... B05C 17/012; B05C 17/0116; B65D 83/0033; A61C 5/062; A45D 34/04
USPC .......................... 222/340, 323, 378, 391, 386
See application file for complete search history.

(56) References Cited

U.S. PATENT DOCUMENTS

| 1,270,835 A | 7/1918 | Jersemann | |
| 4,664,299 A * | 5/1987 | Goncalves | A45D 19/02 222/327 |
| 5,626,473 A | 5/1997 | Muhlbauer et al. | |
| 6,427,878 B1 | 8/2002 | Greiner-Perth et al. | |
| 7,972,075 B2 * | 7/2011 | Tajima | A45D 34/04 401/265 |

FOREIGN PATENT DOCUMENTS

| DE | 3520523 A1 | 12/1986 |
| DE | 9419200 U1 | 5/1996 |

(Continued)

*Primary Examiner* — Nicholas J Weiss
(74) *Attorney, Agent, or Firm* — Global IP Counselors, LLP

(57) ABSTRACT

A dispensing apparatus for a flowable component includes a storage container having a storage chamber for the reception of the component, a filling opening and a dispensing opening. A piston is displaceably arranged within the storage container in the direction of an expulsion direction. Moreover, dispensing apparatus includes an actuation element by which the piston can be displaced stepwise in the direction of the dispensing opening. After release of the actuation element actuation element is displaced from a final position into a starting position by a spring.

13 Claims, 1 Drawing Sheet

(56) References Cited

FOREIGN PATENT DOCUMENTS

| | | |
|---|---|---|
| EP | 0167878 A1 | 1/1986 |
| EP | 1084765 A2 | 3/2001 |
| FR | 2855504 A1 | 12/2004 |
| GB | 2202733 A | 10/1988 |

\* cited by examiner

DISCHARGING DEVICE

CROSS-REFERENCE TO RELATED APPLICATIONS

This application is a U.S. National stage application of International Application No. PCT/EP2013/073654, filed Nov. 12, 2013, which claims priority to EP Patent Application 12195468.9, filed Dec. 4, 2012, the contents of each of which are hereby incorporated herein by reference.

BACKGROUND

Field of the Invention

The invention relates to a dispensing apparatus for a flowable component.

Background Information

In DE 94 19 200 U1 a dispensing apparatus for a flowable component in the form of a dental mass is described. The dispensing apparatus has a storage container having a storage chamber for the reception of the component, a filling opening and a dispensing opening. It has a piston which is arranged displaceable within the storage container in the direction of a expulsion direction and by means of which the component can be expelled from the storage chamber via the dispensing opening. Moreover, it has an actuation element by means of which the piston can be displaced stepwise in the direction of the dispensing opening. The actuation element and the piston are configured and arranged such that, on an actuation of the actuation element from a starting position into a final position, a displacement is brought about by one step in the direction of the dispensing opening. After releasing the actuation element it is displaced from the final position into the starting position by a spring.

The actuation element of the said dispensing apparatus must be pivotably arranged at the storage container for this purpose, moreover, the spring must be fixed between the storage container and the actuation element in some form and manner.

SUMMARY

In contrast to this it is, in particular the object of the invention to suggest a dispensing apparatus which can be manufactured simply and cost-effectively. In accordance with the invention this object is satisfied by a dispensing apparatus having a storage container, a piston, an actuation element and a spring.

In accordance with the invention the actuation element is arranged at the filling opening and the displacement of the actuation element takes place in the longitudinal direction. In this way, the spring required for the resetting of the actuation element into the starting position can likewise be arranged in the expulsion direction, such that its fixation is, for example, possible between the storage container and the actuation element in a very simple and cost-effective manner.

Moreover, through the arrangement of the actuation element and its actuation direction easy handling is possible. When a grip element is arranged at the storage container the dispensing apparatus can be held such that the trigger finger and the middle finger lie at the grip element and the actuation element is pushed with the thumb from the starting position into the final position. In this way, only a force is exerted in the expulsion direction such that no danger arises that the dispensing opening already oriented at a target point is moved away from the target point by the displacement of the actuation element in an undesired manner. Moreover, through the resetting of the actuation element a spacing between the actuation element in the starting position and the grip element always remain of equal size, such that the capability of handling of the dispensing apparatus is independent of the volume of the component present in the storage chamber. This differentiates the dispensing apparatus of the invention from a common syringe, in which the spacing between a knob of the actuation element and the grip element continuously further decreases with decreasing volume of the components and thus the handling becomes more difficult.

The dispensing apparatus has a storage container having a storage chamber for the reception of the component, a filling opening and a dispensing opening. It has a piston which is arranged displaceable along an expulsion direction within the storage container and by means of which the component can be expelled from the storage chamber via the dispensing opening. Moreover, it has an actuation element by means of which the piston can be displaced stepwise in the direction of the dispensing opening.

The storage chamber, in particular has a circular cross-section which at least sectionally is constant. However, also further cross-sections, such as for example oval, rectangular or quadratic are possible. The cross-section of the storage chamber increases, in particular in the direction of the filling opening such that the piston can be inserted simply and without danger of collision in the storage chamber. In the region of the dispensing opening, the cross-section of the storage chamber can reduce. In this case, in particular the form of the piston corresponds to the extent of the cross-section of the storage chamber in the region of the dispensing opening, such that, apart from a small residual amount, the complete component can be dispensed from the storage chamber. The component, which can, for example be a liquid for the medical field, or also an adhesive in the field of trade-craft is, in particular filled via the filling opening into the storage chamber. However, it is also possible to fill components via the dispensing opening.

The actuation element and the piston are configured and arranged such that, on a displacement of the actuation element from a starting position into a final position, the piston is displaced by one step in the direction of the dispensing opening. This should be understood such that the piston is displaced for a predetermined unit in the direction of the dispensing opening during one step and in this way a predetermined amount of the component is dispensed. A step-wise displacement of the piston should be understood in the manner such that the piston can be displaced a plurality of times, this means at least twice per step. The piston is, in particular always displaced the same distance for the individual steps. However, it is also possible that the piston is not always equally displaced.

After releasing the actuation element it is displaced back by a spring from the final position into the starting position. In this connection, the piston remains standing in its achieved position and only the actuation element is pushed back. In this way a relative movement between the piston and the actuation element takes place. The pushing back of the piston is, in particular prevented by frictional forces between a piston circumferences of the piston and an inner wall of the storage chamber. After the pushing back of the actuation element into the starting position the dispensing apparatus is ready to dispense a further defined amount of the component.

The dispensing apparatus is, in particular configured for dispensing a total of between 0.5 and 5 ml, in particular between 1 and 3 ml, for example in 4 to 8 steps. Moreover, it is configured for the purpose of only being used once and subsequently being disposed of.

In an embodiment of the invention the piston has at least two feed surfaces spaced apart in the expulsion direction and the actuation element has at least one actuation surface. The feed surface and the actuation surface are configured and arranged such that, on a displacement of the actuation element from the starting position into the final position, a force is transmitted onto the piston in the direction of the dispensing opening via the actuation surface and the feed surface. In this way, a particularly simple construction of the dispensing apparatus is possible. The feed surfaces are, in particular arranged sectionally transverse with respect to the expulsion direction and specifically at least sectionally perpendicular to the expulsion direction.

In an embodiment of the invention the actuation element has an actuation arm which is oriented in the direction of the dispensing opening and in this way generally in the expulsion direction. The actuation arm has the actuation surface such that the force for displacing the piston in the direction of the dispensing opening is transmitted via the actuation arm and the actuation surface onto the piston. In this way, a simple and cost-effective construction of the actuation element is possible. The actuation element has, in particular two diametrically oppositely lying actuation arms. In this way, a symmetric introduction of force onto the piston is possible, such that this can be displaced uniformly and without the danger of tilting or canting.

In an embodiment of the invention the actuation arm is flexibly transverse to the expulsion direction. It has a guiding surface, which cooperates with a repelling surface of the piston such that the actuation arm is bent transverse to the expulsion direction on a displacement from the final position in the direction of the starting position such that a relative movement between the piston and the actuation element is enabled. In this way, the required decoupling of the actuation arm and the piston for enabling the relative movement of the two parts can be implemented particularly simply. The guiding surface is, in particular inclined such that at its end in the direction of the dispensing opening it has a smaller spacing with respect to the inner wall of the storage chamber than at its opposing end. The repelling surface is, for example, configured as a partly surrounding edge at the inner wall of the storage chamber. As soon as the actuation element is released, the actuation element is thus impinged with a force by the spring in the direction of the starting position. Through the cooperation of repelling surface of the piston and the guiding surface of the actuation arm this is inwardly bent and can glide past the piston.

However, it is also possible that the piston is flexible and this can additionally or solely deflect in order to enable the required relative movement.

In an embodiment of the invention the piston has an inner piston space open in the direction of the filling opening which inner piston space is bounded transverse to the expulsion direction by a piston jacket. The feed surfaces are formed in the piston jacket and the actuation arm projects into the inner piston space. In this way, a particularly simple assembly of the dispensing apparatus is possible. The actuation arm projects at least for so long into the inner piston space as long as the piston can still be displaced by more than one step. On the last step the actuation arm can, for example, be supported at a boundary of the piston jacket so that it can no longer project into the inner space.

In an embodiment of the invention the piston jacket has a recess, which possesses a feed surface. In this manner, a piston jacket can be manufactured particularly simple. Moreover, little material is required for its manufacture so that it can also be manufactured cost-effectively.

The piston jacket, in particular has two diametrically oppositely disposed recesses which each have a feed surface. In this way, as already described, a symmetric introduction of force into the piston is possible in a simple manner.

In an embodiment of the invention the piston has a surrounding sealing element with respect to the expulsion direction which lies at the inner wall of the storage chamber. In this manner, on the one hand, a seal is achieved between the piston and the storage chamber such that it is effectively ensured that the components are completely dispensed and do not partly adhere at the inner walls of the storage chamber. Moreover, such an airtight sealing of the storage chamber in the direction of the filling opening is achieved such that no air can penetrate into the storage chamber via this path and the components could be damaged thereby. On the other hand, the already described frictional forces between the piston and the storage chamber can be set on a pushing back of the actuation element into the starting position and, in particular increased by means of the sealing element. The sealing element can, in particular be configured as an O-ring of an elastomer.

In an embodiment of the invention the piston has a piston base which terminates the storage chamber in the direction of the filling opening. In this connection, the piston base surroundingly touches the inner wall of the storage chamber. The piston base is made of a different material than the piston jacket. In this way, an ideal material can be used both for the piston base and also for the piston jacket, wherein the material of the piston base is, in particular softer than that of the piston jacket. The piston base can, for example, be manufactured from a so-called thermoplastic elastomer (TPE) and the piston jacket can for example be manufactured from polypropylene (abbreviation PP) or polyamide (abbreviation PA).

The piston is, in particular of one piece design. It is thus composed of a single part and does not have to be assembled from a plurality of parts. In this way, the mounting of the dispensing apparatus is particularly simple. The piston is, in particular configured as a so-called two component injection molded part. Such an injection molded part is manufactured from two different starting materials in a multi-component injection molding process known per se. Thus, the piston base is, for example, manufactured from TPE and the piston jacket of PP or PA.

In an embodiment of the invention the storage container and the spring are of one piece design. In this way, on the one hand, the manufacture of the storage container and the spring is particularly cost-effective, since they can be manufactured in a manufacturing process, in particular by means of an injection molded process. Moreover, particularly few individual parts are required in this way for the dispensing apparatus, whereby the mounting is particularly simple and cost-effective. The storage container and the spring can, for example, be manufactured from PP.

The storage container and the spring are, in particular configured from different materials. In this way, an ideal material can be used both for the storage container and also for the spring. The storage container and the spring are, in particular configured as two component injection molded parts which can likewise be manufactured by means of a multi-component injection molded process from two different starting materials. The storage container can, for example, be manufactured from PP and the spring from PA.

In an embodiment of the invention the actuation element is arranged such that it terminates the filling opening of the storage container. In this way, it can be prevented that foreign matter can penetrate into the inner piston space.

The actuation element, in particular has a groove in which a bulge of the storage container is arranged. In this way, it is effectively prevented that, once an actuation element is plugged onto the storage container, it can slide off of this in an undesired manner. In this connection, the groove is configured such that the bulge is arranged in the groove both in the starting position and also in the final position. The said groove is, in particular configured surrounding. The bulge of the storage container is, in particular configured as a surrounding collar.

In the final position of the actuation element, the bulge, in particular lies at an end flange of the groove oriented in the direction of the dispensing opening. In this manner it is ensured that the actuation element can only be displaced by a predetermined unit in the direction of the dispensing opening. Thus, on a displacement of the actuation element from the starting position into the final position, always the same amount of component can be dispensed. Without such an abutment, the movement of the actuation element would only then be stopped when the spring is stopped. The point at which this happens is, however, not so precisely defined.

The dispensing opening can, in particular be terminated with a cover which can, for example, be manufactured from PP in an injection molded process.

The actuation element can, for example, be manufactured from PP or PA in an injection molded process.

The dispensing apparatus is, in particular provided for the dispensing of only one component. However, it is also possible that two more components are mixed prior to the dispensing within the dispensing apparatus and the mixed components can be dispensed. For this purpose, two or more separate storage chambers can be arranged within the storage container in which different components are contained. The components can be dispensed simultaneously from the storage chambers by means of a piston or a plurality of coupled pistons. The piston or the pistons are actuated as described by an actuation apparatus. For a better mixing of the components a mixer element can be arranged within the dispensing apparatus or it can be possible to plug a mixer element onto the dispensing apparatus.

Further advantages, features and particulars of the invention result with reference to the subsequent description of embodiments, as well as with reference to the drawing in which the same or functionally equivalent elements are provided with identical reference numerals.

BRIEF DESCRIPTION OF DRAWINGS

In this connection there is shown.

DETAILED DESCRIPTION OF EMBODIMENTS

Figure 1:
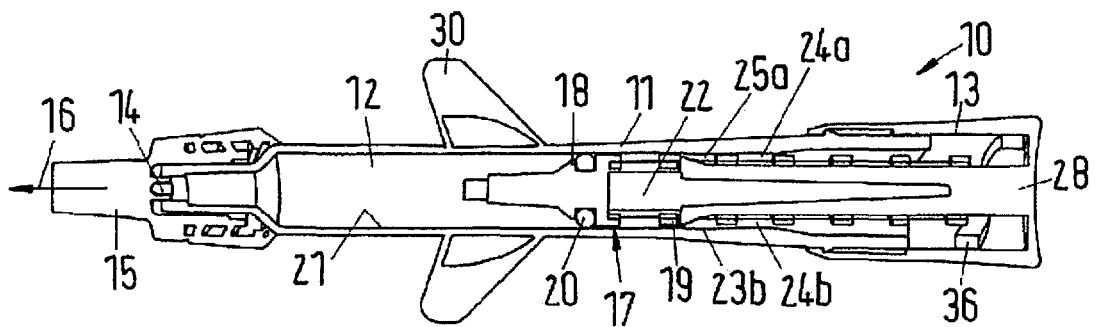
FIG. 1 is a sectional illustration of a dispensing apparatus having an actuation element in a starting position.
Figure 2:
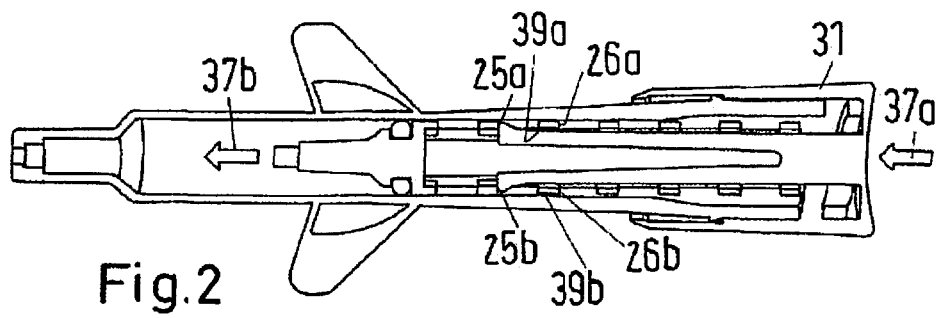
FIG. 2 is the dispensing apparatus of FIG. 1 having the actuation element in a final position.
Figure 3:
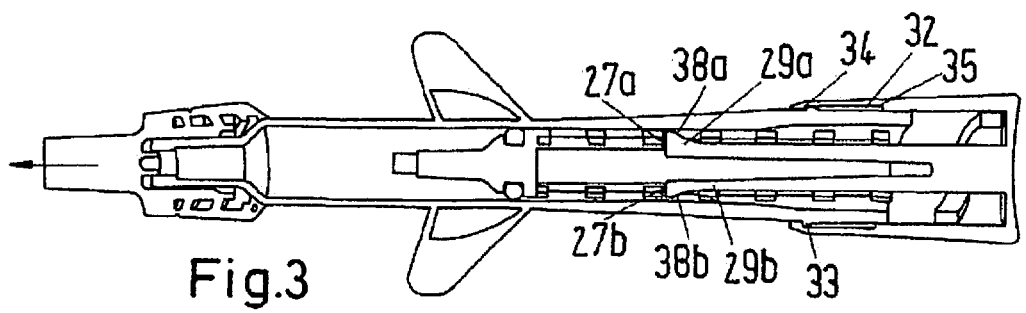
FIG. 3 is the dispensing apparatus of FIG. 1 and FIG. 2 having the actuation element reset again in the starting position.

In accordance with the FIGS. 1, 2 and 3 a dispensing apparatus 10 for a flowable component includes a storage container 11. The storage container 11 has a storage chamber 12 for a flowable component. The storage container 11 has a filling opening 13 and a dispensing opening 14 at its opposite end which dispensing opening can be closed by a removable cover 15. The component can be filled via the filling opening 13 into the storage chamber 12 and after removal of the cover 15 can be dispensed via the dispensing opening 14.

The storage chamber 12 sectionally has a hollow cylindrical inner contour, wherein the storage chamber 12 tapers in the direction of the dispensing opening 14 and expands in the direction of the filling opening 13.

A piston 17 is arranged displaceable along an expulsion direction 16 within the storage container 11. The piston 17 has a piston base 18 which terminates the storage chamber 12 in the direction of the filling opening 13. The piston base 18 has an outer contour extending in the expulsion direction 16 which outer contour corresponds to the inner contour of the storage chamber 12 extending in the expulsion direction 16 in the region of the dispensing opening 14. A sealing element in the form of an O-ring 20 is arranged at the piston base 18 such that it lies around at an inner wall 21 of the storage chamber 12 in a ring-like manner and so seals the piston base 18 with respect to the inner wall 21 of the storage chamber 12.

Moreover, the piston 17 has a piston jacket 19 which adjoins at the piston base 18 in the direction of the filling opening 13. The piston 17 is configured as an injection molded part and in this way is of one piece design. The piston jacket 19 generally has a tubular basic shape and in this way has an inner piston space 22 open in the direction of the filling opening 13. The piston jacket 19 has a total of six pairs of recesses, wherein for reasons of clarity only four recesses 23a, 23b; 24a, 24b of a second and third pair are provided with reference numerals. The recesses 23a, 23b of the second pair are arranged at the same axial position and diametrically lying opposite. The recesses 24a, 24b of the third pair are arranged in the direction of the circumference at the same positions, however, are displaced in the direction of the filling opening 13. The recesses 23a, 23b, 24a, 24b of the piston jacket 19 have feed surfaces 25a, 25b, 26a, 26b oriented in the direction of the dispensing opening 14 which feed surfaces are aligned perpendicular to the expulsion direction 16.

The feed surfaces 25a, 25b, 26a, 26b can cooperate with a first actuation surface 27a and a second actuation surface 27b of an actuation element 28. The actuation element 28 is arranged at the filing opening 13. It has a first actuation arm 29a and a second actuation arm 29b which project into the inner piston space 22 of the piston jacket 19 and each are flexible transverse with respect to the expulsion direction 16. The first and second actuation surface 27a, 27b respectively form the terminal of the first and second actuation arm 29a, 29b in the direction of the dispensing opening 14 and are likewise arranged substantially perpendicular with respect to the expulsion direction 16. The actuation arms 29a, 29b are configured and arranged at the filling opening 13 such that the ends oriented in the direction of the dispensing opening 14 which ends, having the actuation surfaces 27a, 27b, can project into the recesses 23a, 23b, 24a, 24b of the piston jacket 19. In this way, a force can be transmitted onto the feed surfaces 25a, 25b, 26a, 26b and in this way onto the piston 17 in the direction of the dispensing opening 14 via the actuation element 28, the actuation arms 29a, 29b and the actuation surfaces 27a, 27b. The force is applied by a user by displacing the actuation element 28 in the direction of the dispensing opening 14. The said force can be applied, in particular with the thumb of the hand. For supporting the force and fixing the dispensing apparatus 10 the storage container 11 has an outwardly oriented grip element 30. The grip element 30 is configured such that it can be supported, in particular at the trigger finger and the middle finger of the hand.

The actuation element 28 has a cap 31 besides the actuation arms 29a, 29b which cap has a substantially beaker-like basic shape. The cap 31 and in this way the actuation elements 28 are plugged onto the storage container 11 such that the cap 31 and the storage container 11 overlap. In this manner the actuation element 28 closes the filling opening 13 of the storage container 11. The cap 31 and in this way the actuation element 28 have a surrounding groove 32 at its inner side, in which a bulge in the form of a surrounding collar 32 of the storage container 11 is arranged. The groove 32 and the collar 33 are arranged such that the actuation element 28 can be displaced with respect to the storage container 11 and the collar 32 still remains in the groove 32. The actuation element 28 can be displaced with respect to the storage container 11 between a starting position illustrated in the FIGS. 1 and 3, in which the collar 33 contacts at an exit flange 34 oriented in the direction of the filling opening 13, and a final position illustrated in FIG. 2, in which the collar 33 contacts at an end flange 35 oriented in the direction of the dispensing opening 14.

A spring 36 adjoins at the storage container 11 at the filling opening 13 which can apply a force against the expulsion direction 16. The spring 36 is configured as a coil spring and is of one piece design with the storage container 11. The storage container 11 and the spring 36 are configured as a so-called two-component injection molded part, wherein the storage container 11 is made of polypropylene and the spring 36 is made of polyamide. Furthermore, also other types of material are possible.

The spring 36 is biased in the assembled state of the dispensing apparatus such that it exerts a force onto the actuation element 28 which force is oriented opposite to the expulsion direction 16, this means it presses the actuation element 28 in the direction of the starting position. The spring 36 is moreover configured such that it also exerts a force onto the actuation element 28 in the starting position and thereby fixes the actuation element 28 in the starting position.

The design of the recesses 23a, 23b, 24a, 24b in the piston jacket 19 and of the actuation arms 29a, 29b of the actuation element 28 enable a stepwise dispensing of the component via the dispensing opening 14 from the storage chamber 12. This will be described in the following by means of the differences shown in the FIGS. 1, 2 and 3 in more detail.

In FIG. 1 the actuation element 28 is present in the starting position and the actuation arms 29a, 29b dive into the second pair of recesses 23a, 23b such that the actuation surfaces 27a, 27b of the actuation arms 29a, 29b are positioned such that they can cooperate with the feed surface 25a, 25b of the recesses 23a, 23b. From the fact that the actuation arms 29a, 29b dive into the second pair of recesses 23a, 23b and not into the first pair of recesses it is clear that the piston 17 is already displaced by a step in the direction of the dispensing opening 14 and thereby already a defined amount of the component has been dispensed on the storage chamber 12.

Starting from the illustration of FIG. 1, if a further defined amount of the component should now be dispensed, then the cover 15 is initially removed and then the actuation element 28 is impinged with a pressure in the direction of the dispensing opening 14 and in this manner is pushed against the force of the spring 36 with respect to the storage container 11. The said displacement is symbolized in FIG. 2 by the arrows 37a, 37b. In this manner a force is transmitted onto the feed surface 25a, 25b and in this way onto the piston 17 in the direction of the dispensing opening 14 and the piston is displaced in the direction of the dispensing opening 14 which force is applied via the actuation element 28, the actuation arms 29a, 29b and the actuation surfaces 27a, 27b. Through the said displacement of the piston 17 a part of the component is dispensed via the dispensing opening 14. The actuation element 28 can be displaced so far until it arrives in the final position illustrated in FIG. 2, this means that the collar 33 of the storage container 11 abuts at the end flange 35 of the groove 32 of the actuation element 28 and a further displacement of the actuation element and in this way of the piston 17 is made impossible.

If now starting from the illustrated final position of the actuation element 28 illustrated in FIG. 2 a force is no longer applied in the direction of the dispensing opening 14 and in this way set free then it is pressed back again in the direction of the starting position by the spring force of the spring 36 this means it is pushed away from the dispensing opening 14. For enabling a further dispensing of the components, however, the piston 17 should remain in the achieved position such that a decoupling of the actuation element 28 and of the piston 17 becomes necessary. This decoupling is achieved by a cooperation between guiding surfaces 38a, 38b of the actuation arms 29a, 29b and repelling surfaces 39a, 39b of the piston jacket 19 and in this way of the piston 17. The guiding surfaces 38a, 38b adjoin at the actuation surfaces 27a, 27b and are inclined such that they have a smaller spacing with respect to the inner wall 21 of the storage chamber 12 at their end in the direction of the actuation surfaces 27a, 27b than at their opposite end. The repelling surfaces 39a, 39b are configured as edges of the recesses 23a, 23b extending perpendicular to the expulsion direction 16 in the direction of the filling opening 13. As soon as the actuation element 28 is released, the actuation element 28 is impinged by a force as described by the spring 36 in the direction of the starting position. Through the cooperation of repelling surfaces 39a, 39b of the piston 17 and the guiding surfaces 38a, 38b the actuation arms 29a, 29b are bent inwardly, this means away from the inner wall 21 of the storage chamber 12 so far that the actuation arms 29a, 29b can glide past at the piston 17. In this manner, a relative movement between the piston 17 and the actuation element 28 is possible such that the piston 17 remains standing and the actuation element 28 is again displaced backwards into the starting position. The then achieved starting position of the actuation element 28 is illustrated in FIG. 3. This differs from the position illustrated in FIG. 1 only thereby that the actuation arms 29a, 29b now dive into the third pair of recesses 24a, 24b. Starting from this starting position a further defined amount of the component can be dispensed by repeating the described sequence.

Due to the six pairs of recesses in the piston jacket 19 the piston 17 can be displaced in six steps in the direction of the dispensing opening 14, whereby a total of six defined amounts of the component can be dispensed.

In this manner, the piston 17 is likewise not displaced on pushing back the actuation element 28, a sufficiently high friction is required between the piston 17 and the inner wall 21 of the storage chamber 12. For the dispensing apparatus 10 in accordance with the FIGS. 1, 2 and 3 the said friction is ensured by the sealing element in the form of an O-ring 20.

However, it is also possible that the piston base is configured such that it has a sufficiently high friction with respect to the inner wall of the storage chamber without an additional sealing element.

Figure 4:
FIG. 4 is a piston of a dispensing apparatus in a second embodiment.

Such an embodiment of a piston 117 is illustrated in FIG. 4. The piston 117 is generally of equal design to the piston 17 of FIGS. 1, 2 and 3 which is why reference is only made to the differences of the two pistons 17, 117.

The piston 117 is configured as a two-component injection molded part. A piston base 118 is made from a different softer material than a piston jacket 119. The piston base 118 is, for example, manufactured from a thermoplastic elastomer (abbreviation TPE) and the piston jacket 119 is, for example, made of polypropylene (abbreviation PP) or polyamide (abbreviation PA). The piston base 118 has an outer contour which corresponds to the inner contour of the storage chamber such that no additional sealing element is required.

The invention claimed is:

1. A dispensing apparatus for a flowable component, comprising:
    a storage container having a storage chamber for the reception of the component, a filling opening and a dispensing opening;
    a piston arranged so as to be displaceable in an expulsion direction within the storage container and being configured to expel the component from the storage chamber via the dispensing opening;
    an actuation element configured to displace the piston stepwise in a direction of the dispensing opening; and
    a spring configured to act on the actuation element,
    the actuation element and the piston being configured and arranged such that, on displacement of the actuation element from a starting position into a final position, the piston is displaced by one step in the direction of the dispensing opening,
    the actuation element being configured to be displaced by the spring from the final position into the starting position,
    the actuation element being arranged at the filling opening and the displacement of the actuation element being in the expulsion direction,
    wherein the piston has a plurality of feed surfaces spaced apart in the expulsion direction,
    the actuation element has at least one actuation surface, and
    the feed surfaces and the at least one actuation surface are configured and arranged such that, on the displacement of the actuation element from the starting position into the final position, a force is transmitted in the direction of the dispensing opening onto the piston via the at least one actuation surface and the feed surfaces,
    wherein the actuation element has an actuation arm oriented in the direction of the dispensing opening and which has the at least one actuation surface,
    wherein the piston has an inner piston space open in the direction of the filling opening, the inner piston space is bounded transverse to the expulsion direction by a piston jacket,
    wherein the feed surfaces are formed in the piston jacket, and
    the actuation arm projects into the inner piston space.

2. The dispensing apparatus in accordance with claim 1, wherein the actuation arm is flexibly transverse to the expulsion direction and has a guiding surface configured to cooperate with a repelling surface of the piston such that the actuation arm is bent on displacement from the final position into the starting position transverse to the expulsion direction and relative movement is enabled between the piston and the actuation element.

3. The dispensing apparatus in accordance with claim 1, wherein the piston jacket has a recess having one of the plurality of feed surfaces.

4. The dispensing apparatus in accordance with claim 1, wherein the piston jacket has two diametrically oppositely disposed recesses, each having one of the plurality of feed surfaces.

5. The dispensing apparatus in accordance with claim 1, wherein
    the piston has a surrounding sealing element lying at an inner wall of the storage chamber.

6. The dispensing apparatus in accordance with claim 1, wherein the piston has a piston base terminating the storage chamber in the direction of the filling opening and being made from a different material than the piston jacket.

7. The dispensing apparatus in accordance with claim 6, wherein the piston is one piece.

8. The dispensing apparatus in accordance with claim 1, wherein the storage container and the spring are one piece.

9. The dispensing apparatus in accordance with claim 8, wherein the storage container and the spring are made of different materials.

10. The dispensing apparatus in accordance with claim 1, wherein
    the actuation element is arranged so as to close the filling opening of the storage container.

11. The dispensing apparatus in accordance with claim 10, wherein
    the actuation element has a groove in which a bulge of the storage container is arranged.

12. The dispensing apparatus in accordance with claim 11, wherein, in the final position of the actuation element, the bulge lies at an end flange of the groove oriented in the direction of the dispensing opening.

13. A dispensing apparatus for a flowable component, comprising:
    a storage container having a storage chamber for the reception of the component, a filling opening and a dispensing opening;
    a piston arranged so as to be displaceable in an expulsion direction within the storage container and being configured to expel the component from the storage chamber via the dispensing opening;
    an actuation element configured to displace the piston stepwise in a direction of the dispensing opening; and
    a spring configured to act on the actuation element,
    the actuation element and the piston being configured and arranged such that, on displacement of the actuation element from a starting position into a final position, the piston is displaced by one step in the direction of the dispensing opening,
    the actuation element being configured to be displaced by the spring from the final position into the starting position,
    the actuation element being arranged at the filling opening and the displacement of the actuation element being in the expulsion direction, and
    the storage container and the spring being one piece.

* * * * *